United States Patent [19]

Lowther

[11] 4,038,050
[45] July 26, 1977

[54] ELECTRICAL SENSING AND REGENERATING SYSTEM FOR MOLECULAR SIEVE DRIERS

[75] Inventor: Frank Eugene Lowther, Buffalo, N.Y.

[73] Assignee: W. R. Grace & Co., New York, N.Y.

[21] Appl. No.: 694,017

[22] Filed: June 7, 1976

Related U.S. Application Data

[63] Continuation-in-part of Ser. No. 535,282, Dec. 23, 1974, abandoned, and Ser. No. 625,237, Oct. 23, 1975, which is a continuation-in-part of Ser. No. 527,832, Nov. 27, 1974, abandoned.

[51] Int. Cl.² .............................................. B01D 53/04
[52] U.S. Cl. .......................................... 55/18; 55/33; 55/58; 55/161; 55/208
[58] Field of Search ................... 55/58, 29, 31, 33, 34, 55/208, 75, 159, 163, 161, 179, 389, 18, 20, 1, 4, 6, 8; 204/129, 130, 195, 265, 144.5; 210/96

[56] References Cited

U.S. PATENT DOCUMENTS

| 3,188,283 | 6/1965 | Cole | 204/195 X |
| 3,193,985 | 7/1965 | Siggelin | 55/33 |
| 3,474,023 | 10/1969 | Bloch | 204/265 |
| 3,608,273 | 9/1971 | Fabuss et al. | 55/208 X |
| 3,708,956 | 1/1973 | Norback | 55/163 X |
| 3,734,293 | 5/1973 | Biskis | 55/208 X |
| 3,768,649 | 10/1973 | Fleckenstein | 210/96 |

*Primary Examiner*—John Adee
*Attorney, Agent, or Firm*—Arthur P. Savage

[57] ABSTRACT

A fluid drying system comprising a molecular sieve bed of crystalline metal aluminosilicate zeolite particles for removing water from a moisture-laden process stream. The improved apparatus and methods provides means for measuring electrical conductivity of the zeolite particles and generating a signal representative of sorbed water content. Means responsive to the signal is provided for interrupting process fluid flow through the bed at a predetermined bed water content. In the preferred embodiments a high voltage is imposed across the bed for regenerating the bed to separate sorbed water from the zeolite particles.

13 Claims, 4 Drawing Figures

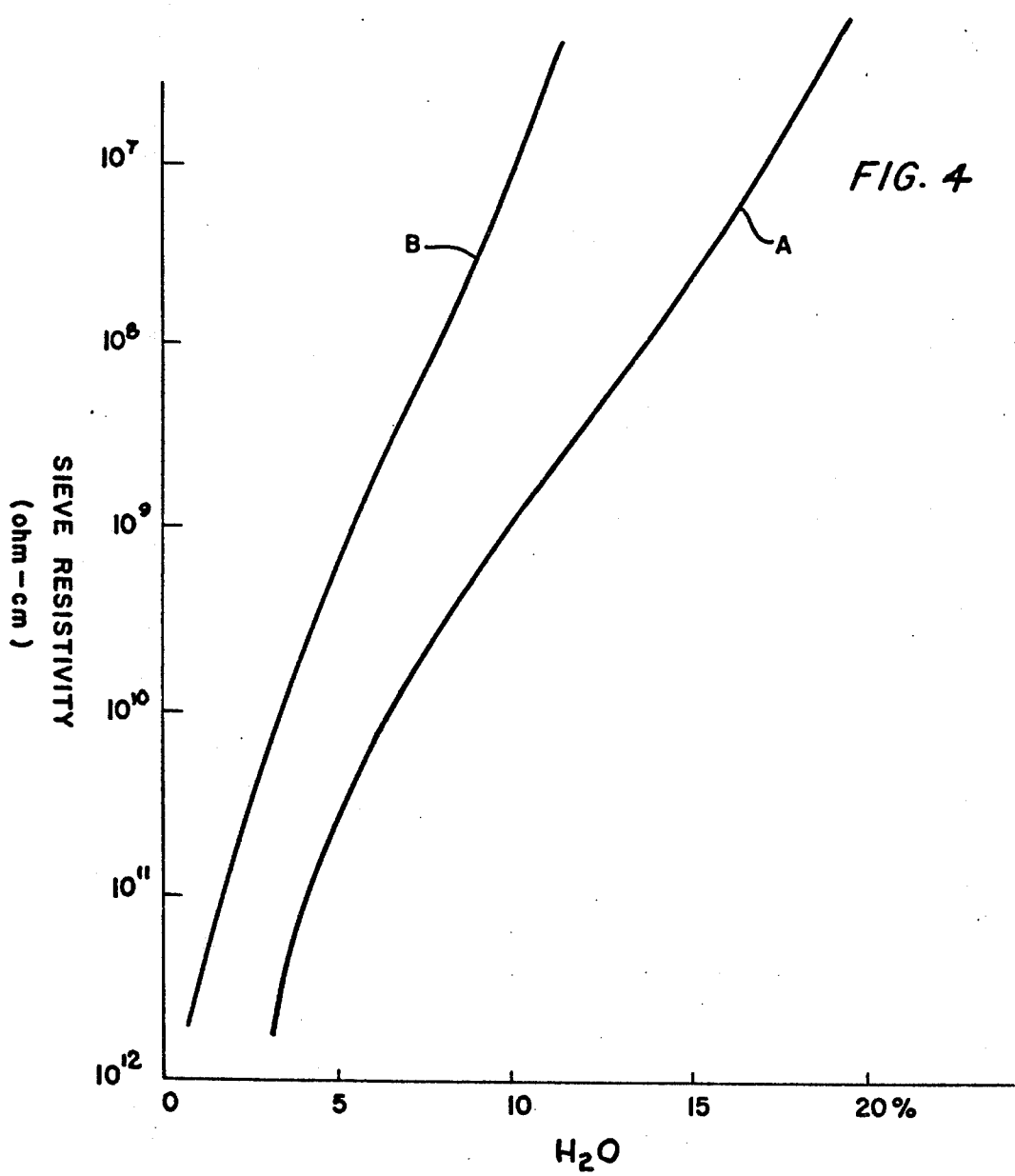

ELECTRICAL SENSING AND REGENERATING SYSTEM FOR MOLECULAR SIEVE DRIERS

This application is a continuation-in-part of applications Ser. No. 535,282 filed Dec. 23, 1974 now abandoned and Ser. No. 625,237 filed Oct. 23, 1975, which is a continuation-in-part of Ser. No. 527,832 filed Nov. 27, 1974 now abandoned.

This invention relates to molecular sieve drying systems. In particular, it relates to methods and apparatus for removing moisture from fluid streams and for regenerating or reactivating moisture-laden zeolite particles of the alkali metal aluminosilicate type. Molecular sieves made from natural or synthetic crystalline alkali-metal alumino-silicates of the zeolite type have been found useful for removing selected components from fluid streams. Drying of fluids such as air, petroleum feedstocks or industrial gases has provided a substantial use for molcular sieve.

Gases can be dried to a water content of a few parts per million. In many systems designed to condition feed to cryogenic plants, the gas must be dried to a fraction of a part per million - low enough to make deriming of heat exchangers a very rare necessity, even when the gas is taken all the way to the liquid phase. This super-drying can be accomplished even when the feed gas is at high temperature because the dewpoints of molecular sieve dehydration are not a function of inlet temperature, and because these unique adsorbents maintain high capacity even when operating at high temperatures, The ability to handle high temperature feed while producing completely dry gas is a unique characteristic of molecular sieve systems. In addition, the performance of molecular sieves is not affected by the degree of saturation of the feed.

The problem of drying large volumes of fluids at a rapid rate is particularly pressing in the operation of petroleum refineries in which large quantities of hydrocarbon fluids are handled daily. The increase in the yield of product which accompanies such reduction in the water content of the charging stock in many instances more than compensates for the cost of drying the charging stock with chemical drying agents. Although the problem of drying hydrocarbon fluids on a continuous basis is a typical large scale application of the present process because of the large volumes of the hydrocarbon streams utilized in the petroleum industry, the process may be used in many fluid streams (whether normally liquid or gaseous) which are are essentially non-reactive with the particular desiccant involved in the process. Thus, moist streams such as air nitrogen, carbon monoxide, carbon dioxide, halogenated hydrocarbon chlorobenzene, and others are nonreactive with appropprr iate inorganic desiccants and may be utilized as feed stocks for molecular sieve drying processes. The sieves are inert to most process fluids and physically stable in normal bed depths even when wet with water.

The desiccant properties of molecular sieves are carried to higher temperatures than those of other adsorbents. Typical capacity is 16.5% at 95° C and 4% even at 230° C. The amount of water adsorbent has little effect on their drying efficiency up to the "break point" (the point where the vapor pressure increases abruptly). Dewpoints below −75° C, even with gases as high as 100° C, may be realized. Molecular sieves dry gases at high superficial velocities even with low relative humidity feed gases. The velocity usually ranges from 10 to 50 m/min with zeolite agents. For drying purposes, smaller-pore-size molecular sieves (3 A) are often employed to reduce coadsorption of other materials.

Synthetic crystalline alkali-metal alumino-silicates of the faujasite type are described in U.S. Pat. Nos. 2,882,243, 2,882,244, incorporated herein by referene.

PRIOR ART REGENERATION METHODS

The exhausted bed must be regenerated to remove the adsorbate in preparation for the next adsorption step. Normally, the main flow will be switched to a second adsorption tower during this regeneration to provide a continuous operation. In the prior art, regeneration may be accomplished in several ways, the choice depending on technical and economic considerations. Regeneration methods in the past have depended on the same principle - the process conditions surrounding the adsorbent are changed to those corresponding to a very low equilibrium capacity. In general, the greater the difference between the equilibrium capacities of adsorption and regeneration, the more rapid and complete the regeneration.

In typical cyclic systems, the adsorbate is removed from molecular sieve beds by heating and purging with a carrier gas. This regenerates the adsorbent and prepares it for the next adsorption cycle. During regeneration, sufficient heat must be available to raise the temperature of the adsorbent, the adsorbate, and the vessel, plus an additional amount to vaporize the liquid and offset the heat of wetting of the molecular sieve surface. In most practical designs, gas temperatures in excess of the adsorbate's boiling point are used to increase the rate of heat input to the system. When regeneration temperatures are considered, it is the bed temperature (the temperature of the molecular sieve beads) that is critical. Bed temperatures in the 200 to 300° C range are usually employed.

After regeneration, a cooling period reduces the molecular sieve temperature to about 15-20° C above the temperature of the stream being processed. This is most conveniently done by using the same gas stream as for heating, but with no heat input. The thermal method involves heating to a temperature at which the adsorptive capacity is reduced to a low level so that the adsorbate leaves the molecular sieve surface and is easily removed by a small stream of purge gas. This can be done at operating pressure, or at a reduced pressure.

The "pressure swing" regeneration method similarly depends on reducing the adsorptive capacity by lowering the pressure at essentially constant temperature.

In another method the adsorbate is removed without changing the temperature or pressure, by passage of a fluid (liquid or gas) containing no adsorbable molecules, and in which the adsorbate is soluble or miscible.

Changing the temperature or pressure by passing of a fluid containing a high concentration of an adsorbable molecule can also effect desorption. Because of this high concentration, these molecules are able to displace material previously adsorbed. In the case of liquids, the resulting mixture is then separated, by distillation, into a saleable product of high purity and the regenerating fluid (which is reused).

Regeneration of a wet molcular sieve bed by electrolysis is disclosed in U.S. Pat. No. 3,474,023 by application of a low DC potential to evolve $H_2$ and $O_2$. Also, application of high frequency electrical energy to effect dielectric heating of the bed particles is shown in U.S. Pat. No. 3,359,707.

It is known that the heat of adsorption of water is aproximately the same as the heat of vaporization. Most regeneration methods consume far in excess of this to remove the adsorbate. In view of the widespread use of molecular sieve adsorption, especially in drying air, hydrocarbon feedstocks and industrial gases, there is a definite need for a sieve regeneration process that is fast, economical and easily controlled.

SUMMARY OF THE INVENTION

A novel regeneration system for a molecular sieve fluid drier has been discovered within moisture is sorbed from a fluid stream by a packed bed of zeolite particles, where it is detected electrically. The system provides methods and means for measuring electrical conductivity of the packed bed and generating a signal representative of moisture content of the bed; comparing the signal with a predetermined value; interrupting the fluid stream through the bed when the predetermined value is exceeded; recharging the bed by removing sufficient sorbed water to regenerate the bed; and reinitiating flow of the fluid stream through the bed.

In the preferred embodiment the system includes a plurality of spaced apart electrodes in contact with the bed; a source of high voltage electrical energy; and means for measuring electrical current flow through the bed between the spaced electrodes. As part of an overall drying system the invention further has means for applying the high voltage energy to the bed between the spaced electrodes to regenerate the bed, and a vacuum or purge gas may be applied to the bed concurrently with the high voltage electrical energy.

The system is useful for zeolite particles, such as Type A, Type L, Type X or Type Y zeolites, having an average particle size of at least 1 $\mu$, and is especially adapted for use with a regeneration sub-system which comprises spaced-apart electrically conducting members having the molecular sieve bed substantially there-between; and electrical means for imposing a recharging voltage of about 0.2 Kv/cm to 10 Kv/cm between the electrically conducting members.

The invention has as an important object a system for gas drying comprising a porous molecular sieve bed comprising crystalline metal alumino-silicate zeolite particles for removing water from a moisture laden gas stream, including means for measuring electrical conductivity of the zeolite particles and generating a signal representative of sorbed water content; means responsive to said signal for interrupting gas flow through the bed at a predetermined bed water content before saturation; and means for regenerating the bed to separate sorbed water from the zeolite particles.

These and other objects and features of the invention will be apparent to a skilled scientist by reference to the following description and in the drawing.

THE DRAWING

FIG. 4 is a graphic plot of electrical resistivity and moisture content for a molecular sieve bed.

DESCRIPTION

Figure 1:
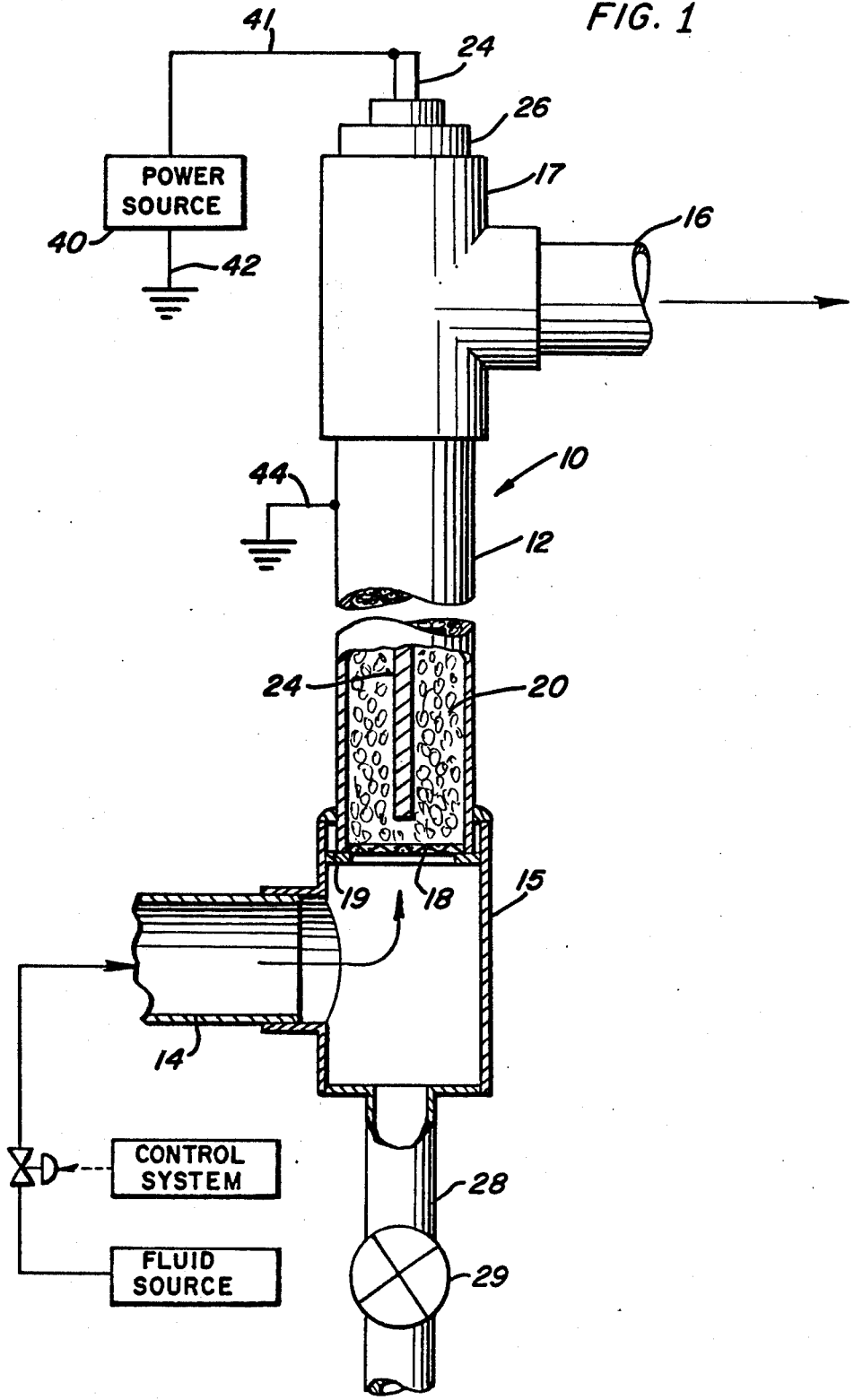
FIG. 1 is a sideview, partially cut away, of 10 typical electro-desorption apparatus, according to the present invention.

The molecular sieve materials consist essentially of crystalline, hydrated metal aluminosilicates with a number of unusual properties. The most important types of molecular sieves are made synthetically, but their structure is similar enough to certain naturally occurring minerals to be classified as zeolites. Although the crystal structures of some of the molecular sieves are quite different (two types, A and X are most important), their significance as commercial adsorbents depends on the fact that in each the crystals contain interconnecting cavities of uniform size, separated by narrower openings, or pores, of equal uniformity. When formed, this crystalline network is full of water, but with moderate heating, the moisture can be driven from the cavities without changing the crystalline structure. This leaves the cavities with their combined surface area and pore volume available for adsorption of water or other materials. The process of evacuation and refilling the cavities may be repeated indefinitely, under favorable conditions.

With molecular sieves close process control is possible because the pores of the crystalline network are uniform rather than of varied dimensions, as is the case with other adsorbents. With this large surface area and pore volume, molecular sieves can make separations of molecules, utilizing pore uniformity, to differentiate on the basis of molecular size and configuration.

Molecular sieves are crystalline, metal aluminosilicates with three dimensional network structures of silica and alumina tetrahedra. This very uniform crystalline structure imparts to the Molecular Sieves properties which make them excellent desiccants, with a high capacity even at elevated temperatures. Some molecular sieves, in addition to this high adsorptive capacity, have the ability to indicate relative humidity by a change in color, which can be utilized to determine the point where reactivation is required.

The crystalline metal alumino-silicates have a three dimensional interconnecting network structure of silica and alumina tetrahedra. The tetrahedra are formed by four oxygen atoms surrounding a silicon or aluminum atom. Each oxygen has two negative charges and each silicon has four positive charges. This structure permits a sharing arrangement, building tetrahedra uniformly in four directions. The trivalency of aluminum causes the alumina tetrahedron to be negatively charged, requiring an additional cation to balance the system. Thus, the final structure has sodium, potassium, calcium or other cations in the network. These charge balancing cations are the exchangeable ions of the zeolite structure.

In the crystalline structure, up to half of the quadrivalent silicon atoms can be replaced by trivalent aluminum atoms. Zeolites containing different ratios of silicon to aluminum ions are available, as well as different crystal structures containing various cations.

In the most common commercial zeolite, Type A, the tetrahedra are grouped to form a truncated octahedron with a silica or alumina tetrahedron at each point. This structure is known as a sodalite cage.

When sodalite cages are stacked in simple cubic forms, the result is a network of cavities approximately 11.5A in size, accessible through openings on all six sides. These openings are surrounded by eight oxygen ions. One or more exchangable cations also partially block the face area. In the sodium form, this ring of oxygen ions provides an opening of 4.2A in diameter into the interior of the structure. This crystalline structure is represented chemically by the following formula:

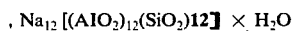

, $Na_{12}[(AlO_2)_{12}(SiO_2)12]$ × $H_2O$

The water of hydration which fills the cavities during crystallization is loosely bound and can be removed by moderate heating. The voids formerly occupied by this water can be refilled by adsorbing a varity of gases and liquids. The number of water molecules in the structure (the value of X) can be as great as 27.

The sodium ions which are associated with the aluminum tetrahedra, tend to block the openings, or conversely may assist the passage of slightly oversized molecules by their electrical charge. As a result, this sodium form of the molecular sieve, which is commercially called 4A, can be regarded as having uniform openings of approximately 4A diameter.

Because of their base exchange properties, zeolites can be readily produced with other metals substituting for a portion of the sodium.

Among the synthetic zeolites, two modifications have found particularly useful in industry. By replacing a large fraction of the sodium with potassium ions, the 3A molecular sieve is formed (with openings of about 3A). Similarly, when calcium ions are used for exchange, the 5A (with approximately 5A openings) is formed.

The crystal structure of the Type X zeolite is built up by arranging the basic sodalite cages in a tetrahedral stacking (diamond structure) with bridging across the six-membered oxygen atom ring. These rings provide opening 9–10A in diameter into the interior of the structure. The overall electrical change is balanced by positively charged cation(s), as in the Type A structure. The chemical formula that represents the unit cell of Type X molecular sieve in the soda form is shown below:

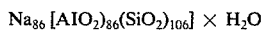
$Na_{86} [AlO_2)_{86}(SiO_2)_{106}] \times H_2O$

As in the case of the Type A crystals, water of hydration can be removed by moderate heating and the voids thus created can be refilled with other liquids or gases. The value of X can be as great as 276.

A prime requisite for any adsorbent is the possession of a large surface area per unit volume. In addition, the surface must be chemically inert and available to the required adsorbate(s). From a purely theoretical point of view, the rate at which molecules may be adsorbed, other factors being equal, will depend on the rate at which they contact the surface of adsorbent particles and the speed with which they diffuse into particles after contact. One or the other of these factors may be controlling in any given situation. One way to speed the mass transfer, in either case, is to reduce the size of the adsorbent particles.

While the synthetic crystals of zeolites are relatively small, e. g., 0.1 $\mu$ to 10 $\mu$, these smaller particles may be bonded or agglomerated into larger shapes. Typical commercial spherical particles have an average bonded particle size of 100 $\mu$ to 500 $\mu$ (4 $\times$ 12 mesh). Other molecular sieve shapes, such as pellets (1–3 mm diameter), Rashing rings, saddles, etc., are useful for continuous sorption processes. The preferred molecular sieve materials are Type A, L, X and Y zeolites or mixtures of these zeolites, having an average particle size of about 1 $\mu$ to 10 $\mu$ for powder or 100 $\mu$ to 500 $\mu$ for bonded particles.

Referring to FIG. 1 of the drawing, a fluid drying apparatus 10 is shown partially cut away. A vertical cylindrical vessel 12 provides a drying chamber. Fluid to be dried is introduced to chamber 12 through fluid inlet means comprising conduit 14 and T-connection 15. Screen 18 is supported at the lower end of vessel 12 by annular ring 19. Screen 18 may be fabricated of metal or suitable material having sufficient strength to support a bed of dielectric absorbent particles 20 such as zeolite molecular sieve particles. A concentric metal electrode 24 is inserted through vessel 12 in contact with particles 20. Electrode 24 is held in fixed position by electrically insulated bushing 26 connected to T-connection 17. Electrode 24 is operatively connected to power source 40 by electrical lead 41. The power source is connected to ground by electrical lead 42.

Vessel 12 may be constructed of an electrically conducted material such as steel to provide an electrical path for direct contact with particulate bed 20. Vessel 12 may be connected to ground by electrical lead 44. Means for draining the vessel 12 may be provided by fluid conduit 28 having valve 29 disposed therein. Conduit 14 is provided with means, such as a control valve, for interrupting inlet fluid flow during regeneration. Discharge outlet 16 can be connected alternatively to a downstream utilization or vented to atmosphere during regeneration to remove sorbate vapor.

The electrodesorption regeneration method may be used with a dry purge gas passing through the bed during regeneration, or a vacuum can be maintained by suitable pressure seals and valving of the system.

The drying cell configuration may be adapted to different process requirements. High gas throughput is obtainable for many processes. Condensation of water vapor or desorbed liquid may require a gravity liquid flow through the particulate bed to a drainport, as shown in FIG. 1. In other systems, the electrodesorbed component is removed only in the vapor phase.

The vessel 12 may be constructed of electrically insulating material such as polyvinyl chloride (PVC), nylon phenolic, acrylic, or ABS resin, glass, glass-lined steel, or wound fiberglass/resin. Where a case electrode is employed, the shell may be metal or metal-lined.

Electrodes may be constructed of sintered metal powder, steel wool, drilled carbon or other foraminous electrically conducting materials. Powdered sieve may be contained by porous metal screen/wool electrode structures.

The physical state of the bed while drying a fluid need not be the same as during the electrodesorption step. The degree of compaction can vary widely within the operable limits of the system. During regeneration, the zeolite particles should be maintained in a physical state to permit electrical flow from a first electrode to a second electrode through an electrical path from particle to particle. Ordinarily, a void volume of less than 50 vol% is suitable to achieve this condition. Loosely-packed fluid-permeable molecular sieve beds have a macro-porosity or void volume of about 30-40 vol%. It is believed that the flow of electrical current takes place on the particle surface due to mobility of the alkali metal ion in the sorbed water phase.

In a preferred practice of my invention the adsorbent bed is regenerated using the electrodesorbtion technique set forth in my copending application Ser. No. 625,237 filed Oct. 23, 1975. As set forth in that application, the adsorbent bed is economically and rapidly regenerated by application of electrical energy to the bed at a preferred voltage of about 0.05 to 500 kv/cm, a current density of about 0.01 to 100 microamps/cm$^2$, and a frequency of about 0 to 10$^3$Hz.

A comparison of my preferred electrodesorbtion method of regeneration with a typical prior art method of regeneration such as thermal reactivation reveals the efficient use of energy achieved by electrodesorbtion.

For example, the heat of adsorbtion and desorbtion of water as vapor on Type A sodium molecular sieve (NaA) is about 1000 cal/g of H$_2$O at 20° C. The theoretical heat of desorbtion when water is desorbed in the liquid phase may be calculated as the heat of desorbtion less the heat of vaporization of water that is 1000 less 540 or about 460 cal/g. Accordingly, if water is desorbed from the molecular sieve mostly in the form of liquid water, the minimum heat for regeneration can theoretically approach 460 cal/g. However, it is observed that the energy required to electrodesorb molecular water from NaA at a reasonable rate is about 1 to 2 times the heat of desorbtion of water as vapor, that is, 1000 to 2000 cal/gH$_2$O.

In contrast, the amount of heat required to desorb water via a conventional heating process as vapor from NaA is equal to the heat of desorbtion, plus the heat of vaporization, plus the heat required to the adsorbent bed and desorbed water vapor to an elevated regeneration temperature at which desorbtion will occur at a reasonable rate.

The following typical example clearly illustrates the saving of energy which is obtained through use of my novel process. Assume the following:

| | |
|---|---|
| Heat capacity of H$_2$O vapor | 0.5 cal/g/° C |
| Heat capacity of H$_2$O liquid | 1 cal/g/° C |
| Heat of vaporization of H$_2$O | 540 cal/g |
| Heat of Adsorbtion of H$_2$O on NaA | 1000 cal/g |
| Bulk density of NaA | 0.69 g/cm$^3$ |
| Specific heat of NaA | 0.25 cal/g/° C |
| Saturation level of H$_2$O adsorbed on NaA | 0.20 g/g |
| Regeneration temperature | 230° C |

A typical adsorbtion column having a diameter of 183 cm and a height of 305 cm and a volume of 8.02 × 10$^6$ cm$^3$ will contain 5.53 × 10$^6$g of NaA. It is desired to dry in air to a dew point of +10° C or 3000 ppm H$_2$O. It is assumed that to obtain air of this degree of dryness, the bed is placed on an adsorbtion cycle until 5% of its saturated capacity is achieved. Therefore, the amount of H$_2$O on the bed is equal to:

1. $0.05 \times 0.2 \times 5.53 \times 10^6 = 0.6 \times 10^5$g

If the heat lost to radiation and convection during a typical 2 to 4 hour regeneration cycle is neglected, the amount of heat required to heat the NaA in the bed to 230° C from 20° is equal to:

2. $0.25 \times (230-20) \times 5.53 \times 10^6 = 2.9 \times 10^8$cal

The heat of desorbtion as water vapor is equal to:

3. $1000 \times 0.6 \times 10^5 = 0.6 \times 10^8$cal

The heat necessary to raise the temperature of the water vapor to the regeneration temperature is equal to:

4. $0.5 \times 0.6 \times 10^5 \times (230-20) = 6.3 \times 10^6$cal

The total heat required for conventional regeneraton of the bed is the sum of items (2), (3) and (4) above or about (5) $3.6 \times 10^8$cal.

In contrast to the above, it is found that the heat required to regenerate the same bed using the electrodesorbtion method is about one to two times the heat of adsorbption as liquid water. Assuming the amount of energy required by my process to be twice the heat of adsorption of water vapor, the amount of heat required to regenerate the bed by electrodesorbtion is equal to:

6. $2 \times 1000 \times 0.6 \times 10^5 = 1.2 \times 10^8$cal

Comparing the value (5) above with (6), the energy saving advantage obtained using electrodesorbtion may be expressed as follows:
$(1.2 \times 10^8 / 3.6 \times 10^8) \times 100 = 33.3\%$ That is, electrdesorbtion utilizes about one-third the heat required to regenerate a molecular sieve drying bed using a standard thermal reactivation technique.

From the above it is seen that from an energy standpoint electrodesorbtion is considerably more efficient than conventional thermal methods. However, more importantly, it is observed that the time required to achieve regeneration using electrodesorbtion is several times less than that required by thermal means. For example, in the bed described above it is found that about 3 hours are required to achieve satisfactory regeneration at 230° C. Using electrodesorbtion it is estimated that satisfactory regeneration may be obtained in as little as 3 minutes. These rapid regeneration times permit the use of much smaller beds in that the size of the beds is no longer governed by lengthy reactivation times.

While the mechanism of electro-desorbtion of wet zeolites is not completely understood, it is believed that the water is first desorbed as a liquid and vaporized from a thin electrolyte film by energy dissipated in the film as heat during application of high voltage. As water is removed from the particles by desorption and evaporation, the bulk resistivity increases. As set forth above, at a predetermined moisture content, as measured by bed conductivity, the regeneration step is terminated and the drying cycle is continued.

To facilitate a uniform rate removal of water, the regeneration step may be carried out under controlled conditions, such as constant current. As sorbed water is removed from the bed, electrical conductivity decreases, which requires an increase in voltage to maintain the desired current. The current density is preferably maintained at a value of about 0.01 to 100 $\mu$a/cm$^2$ (microamperes per square centimeter), with optimum performance for most zeolites being obtained under constant current conditions in the range of 1 to 10 $\mu$a/cm$^2$. Currents as low as 0.001 $\mu$a/cm$^2$ or as high as 1 a/cm$^2$ are feasible. The above current density values are based on uniformly-sized electrodes. It is understood that different maximum and minimum values may be applied to electrically different areas.

For reactivating moisture-loaded metal alumino silicates, the voltage gradient preferably is about 0.2 to 10 Kv/cm, with best results being obtained in the 0.5 to 2 Kv/cm range. However, it is possible to use voltages up to the electrical breakdown of the strongest dielectric zeolite (up to 500 Kv/cm).

The bulk resistivity ($\rho$) of zeolite particles is measured in a packed bed having the particles in contact with one another and completely filling the space between uniformly shaped parallel conductors. The measured resistance (R) is expressed as R=$\rho$l/A, where $\rho$ is the bulk resistivity (ohms-cm$^2$/cm), 1 is the interelectrode distance (cm) and A is the cell cross-sectional area (cm$^2$).

Current density is a function of bulk resistivity, applied voltage and interelectrode distance, according to the equation:

$$\frac{I}{A} = 1/\rho \, (E/l)$$

where $I/A$ = current density (amperes per cm$^2$)

As moisture content of a sieve bed increases, the conductivity increases ($\rho$ decreases) and more current flows for a given field strength (E/1). In order to maintain constant current during water removal, the electrical field is increased proportionally to conductivity. Thus, when batch reactivation is started, a relatively low voltage gradient is applied and increasing voltage is applied as the water is driven off. The final voltage may be as high as ten times the initial value ($E_f = 10 \times E_o$).

The power supply may provide a continuous DC potential, pulsed DC, a square wave or sinusoidal wave of alternating current. Relatively low frequencies of 0 to 60 Hz are preferred; however, the skin conductance phenomenon is efficacious at higher frequencies, for instance 400 Hz or as high as $10^3$Hz. Radio frequencies, such as produced by a HV generator (about $10^7$Hz), cause overheating of the dielectric sieve adsorbent and are not as efficient in energy consumption as the preferred lower frequencies. DC and very low frequency (0–60H$_z$) power supplies are preferred because of the large power factors achieved, as compared to HF generators or other relatively high frequency sources. By employing such electrical supplies, the heating may be confined largely to electrolytic film or surface layer of the adsorbent crystallite structure without heating the body of the adsorbent itself.

Figure 2:
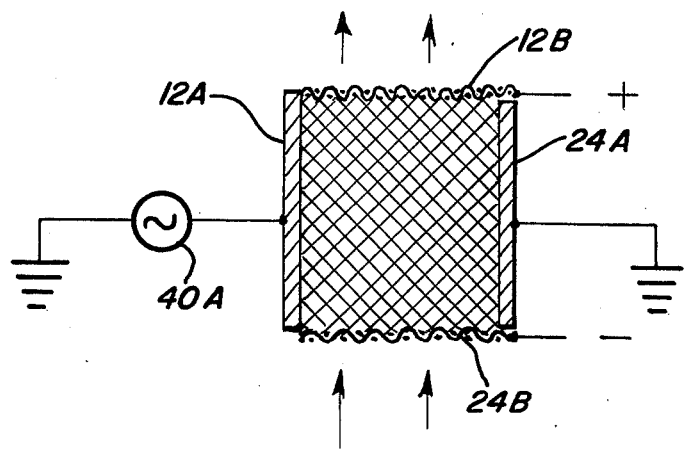
FIGS 2 and 3 are schematic representations of alternative embodiments.

While the measuring electrodes may be integral with regenerating electrodes, a separate set may be provided for each function, as shown in FIG. 2. Electrodes 12A and 24A are connected to a source of high voltage alternating current 40A which is energized in response to a signal derived from a DC current between foraminous screen measuring electrodes 12B and 24B. The measuring current is parallel to the fluid flow, while the regenerating current is transverse. It is understood that these functions may be transposed.

The same source of electrical energy may be employed for both moisture measurement and regeneration. Since ½ to 1 minute or longer is ordinarily required at full power to reactivate a moisture-laden bed, a short high voltage pulse may be used for moisture measurements without substantial heating of the bed. For instance, in one case tested a source of 20 KV-DC was applied to a molecular sieve bed during the drying cycle to measure leakage current.

Figure 3:
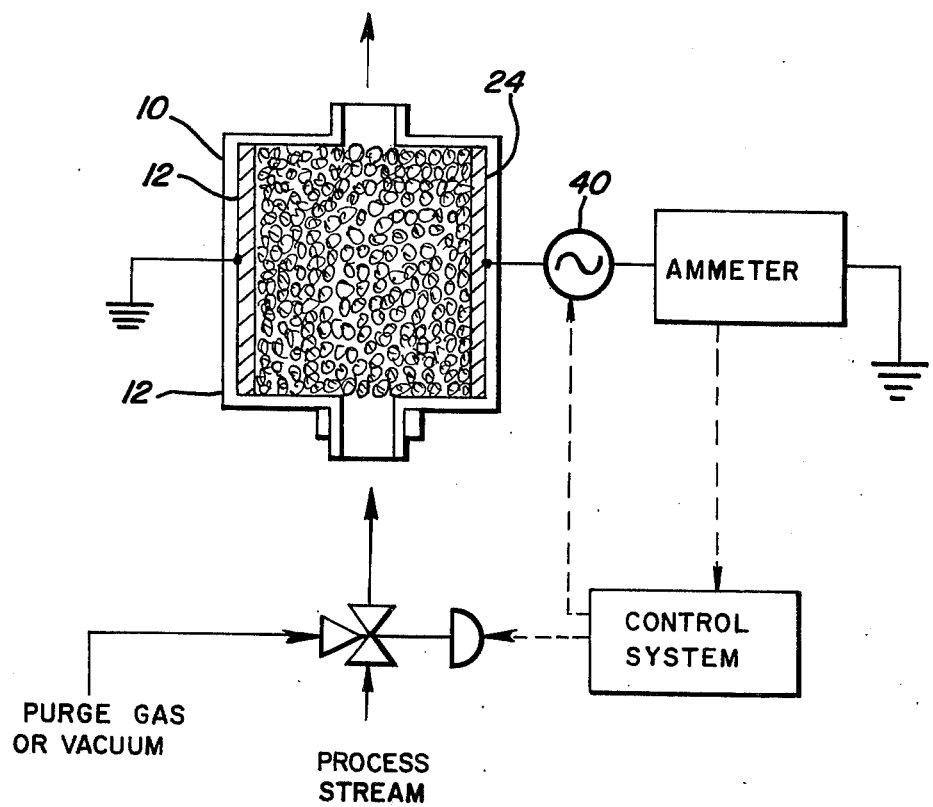

A typical integral electrode system is shown in FIG. 3 wherein a regeneration type molecular sieve apparatus 10 comprising electrically insulated vessel 10 enclosed a molecular sieve bed. Spaced electrodes 12 and 24 are connected to power source 40. An ammeter in series connection measures the electrical current and generates a signal representative of moisture content in the packed particles between the electrodes. A control system, shown in block diagram, is responsive to this signal to operate a valve to interrupt the process stream during degeneration. Under command from the control system the power source may be operated to apply full regeneration potential across the bed through the electrodes sufficient to effect regeneration. During this part of the cycle a purge gas or vacuum may be applied to the vessel 12. When the ammeter signal indicates that moisture has been removed to the desired level, the control system than initiates the drying cycle and returns the power supply to a sensing mode.

The activation or regeneration cycle may be controlled or terminated by pre-set timer, dew-point measurements in the outlet purge gas, bed electrical resistivity signal, regeneration energy consumption, or otherwise.

The moisture-sensing current may be a continuous wave or intermittent pulse type of current. Pulse frequency and duration as well as voltage may be selected to inter-connect the moisture-sensing circuitry with the other functions of the control system. Sequencing of regeneration equipment and of fluid handling equipment may be controlled by a central control module or on - line process computer. These functions are selected according to the process requirements.

It is understood that certain elements of the apparatus may perform multiple functions; for instance, the electrodes for sensing bed moisture may also be employed at high voltage for regenerating the bed. This may require switching the power supply in a known manner.

The moisture-sensing current may itself provide the signal representative of moisture content or a transmitting ammeter instrument may convert this current to a desired electrical, mechanical or fluid signal to represent the value. The signal is compared with a predetermined value to initiate the regeneration cycle for periodically removing water from the molecular sieve bed.

By employing direct low-frequency (0–1000 Hz) electrical energy for removing the absorbate, regeneration can be effected in a time span which is a very small fraction of the time elapsed in loading the molecular sieve during the sorption cycle. Whereas a typical gas drying system may require more than 2 hours to reach moisture capacity (break point), the same amount of water may be removed from the desiccant in about 1 minute or less, which gives a regeneration time less then 1% of the sorption time.

In FIG. 4 a plot of electrical resistivity vs. moisture content is given for two different cell configurations. The data for curve A were obtained using porous screen No. 18 stainless disc electrodes in a cylindrical acrylic plastic tube with a bed 3.2 mm. in diameter and 28 cm long. The particles were 4–5A type x Davison Grade 714 zeolite (8 × 12 mesh). The air flow through the packed bed was 53 l/min (STP) with an inlet water content of 2500 ppm and outlet content of about 2 ppm. The sieve adsorbs about 6.8% $H_2O$ per hour under ambient conditions. Electrical measurements between spaced end electrodes were made using a DC potential of + 18.5 VDC applied with the amode in the downstream position. The upswing in resistivity shows the bed approaching moisture saturation, requiring regeneraton.

Curve B shows the relationship center rod-case electrodes as depicted in FIG. 1.

While the invention has been demonstrated by particular examples, there is no intent to limit the inventive concept except as set forth in the following claims.

What is claimed is:

1. A gas drying system comprising:
   a. an absorbent bed of zeolite particles;
   b. a plurality of spaced apart electrodes in contact with the bed;
   c. means for measuring electrical current flow through the bed between the spaced electrodes and generating a signal representative of adsorbed water content;
   d. means responsive to signal for interrupting gas flow through the bed at a predetermined bed water content; and;
   e. means for applying electrical energy to the bed between the spaced electrodes to regenerate the bed, said electrical energy being provided by said means at a voltage gradient of about 0.05 to 500 Kv/cm, a current density of about 0.001 microamps to 1 amp/cm² and a frequency of 0 to 10³Hz.

2. The system of claim 1 wherein means are provided to apply vacuum to the bed during regeneration.

3. The system of claim 1 wherein means are provided to pass dry purge gas through the bed during regeneration.

4. The system of claim 1 wherein said means for applying electrical energy provides a voltage gradient of about 0.2 to 10 Kv/cm and a current density of 0.01 to 100 microamps/cm².

5. A process for drying a gas stream which comprises:
   a. passing a moisture containing gas stream through a bed of zeolite particles to adsorb water from said gas;
   b. measuring electrical conductivity of the zeolite bed to determine the content of adsorbed water therein;
   c. interrupting said gas stream when the water content of said bed has reached a predetermined level; and
   d. regenerating said bed to remove adsorbed water by application of electrical energy to said bed, said electrical energy being applied at a voltage gradient of about 0.05 to 500 Kv/cm, a current density of about 0.001 microamps to 1 amp/cm², and a frequency of about 0 to 10³ Hz.

6. The process of claim 5 wherein vacuum is applied to said bed during regeneration.

7. The method of claim 5 wherein purge gas is passed through said bed during regeneration.

8. The method of claim 5 wherein subsequent to the regeneration step the process is repeated.

9. The process of claim 5 wherein the frequency is 50 to 60 Hz.

10. The process of claim 5 wherein said gas is air.

11. The process of claim 5 wherein said current density is about 0.01 to 100 microamps/cm².

12. The process of claim 5 where said voltage gradient is about 0.5 to 2 Kv/cm.

13. The process of claim 5 wherein said electrical energy is applied at a voltage gradient of about 0.2 to 10 Kv/cm and a current density of about 0.01 to 100 microamps/cm².

* * * * *